US007888303B2

(12) United States Patent
Tjelta et al.

(10) Patent No.: US 7,888,303 B2
(45) **Date of Patent: *Feb. 15, 2011**

(54) SOLIDIFICATION MATRIX

(75) Inventors: Brenda L. Tjelta, St. Paul, MN (US); Lisa M. Sanders, Eagan, MN (US); Michael E. Besse, Golden Valley, MN (US)

(73) Assignee: Ecolab Inc., Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/969,411

(22) Filed: Jan. 4, 2008

(65) Prior Publication Data

US 2008/0274942 A1 Nov. 6, 2008

Related U.S. Application Data

(63) Continuation-in-part of application No. 11/800,286, filed on May 4, 2007.

(51) Int. Cl.
*A61K 7/50* (2006.01)

(52) U.S. Cl. ........................ 510/191; 510/224; 510/445

(58) Field of Classification Search ................. 510/191, 510/224, 445
See application file for complete search history.

(56) References Cited

U.S. PATENT DOCUMENTS

| | | | | |
|---|---|---|---|---|
| 3,048,548 | A | 8/1962 | Martin et al. | |
| 3,334,147 | A | 8/1967 | Brunelle et al. | |
| 3,442,242 | A | 5/1969 | Laskey et al. | |
| 4,595,520 | A | 6/1986 | Heile et al. | |
| 4,618,914 | A | 10/1986 | Sato et al. | |
| 4,680,134 | A | 7/1987 | Heile et al. | |
| RE32,762 | E | 10/1988 | Katzmann et al. | |
| RE32,818 | E | 1/1989 | Fernholz et al. | |
| 4,830,773 | A | 5/1989 | Olson | |
| 4,971,714 | A | 11/1990 | Lokkesmoe et al. | |
| 5,152,910 | A | 10/1992 | Savio et al. | |
| 6,150,324 | A | 11/2000 | Lentsch et al. | |
| 6,156,715 | A | 12/2000 | Lentsch et al. | |
| 6,177,392 | B1 | 1/2001 | Lentsch et al. | |
| 6,258,765 | B1 | 7/2001 | Wei et al. | |
| 6,262,010 | B1 * | 7/2001 | Emery et al. | 510/446 |
| 6,410,495 | B1 | 6/2002 | Lentsch et al. | |
| 6,583,094 | B1 | 6/2003 | Lentsch et al. | |
| 6,638,902 | B2 | 10/2003 | Tarara et al. | |
| 6,653,266 | B2 | 11/2003 | Wei et al. | |
| 6,660,707 | B2 * | 12/2003 | Lentsch et al. | 510/445 |
| 6,831,054 | B2 | 12/2004 | Lentsch et al. | |
| 7,087,569 | B2 | 8/2006 | Lentsch et al. | |
| 7,094,746 | B2 | 8/2006 | Lentsch et al. | |
| 2005/0233920 | A1 * | 10/2005 | Stolte et al. | 510/147 |

FOREIGN PATENT DOCUMENTS

| | | |
|---|---|---|
| JP | 2000-199178 | 7/2000 |
| JP | 2004-204016 | 7/2004 |

OTHER PUBLICATIONS

International Search Report and Written Opinion of international application No. PCT/IB2008/050825, mailed Sep. 22, 2008, 13 pp.

* cited by examiner

*Primary Examiner*—Milton I Cano
*Assistant Examiner*—M. Reza Asdjodi
(74) *Attorney, Agent, or Firm*—Faegre & Benson LLP

(57) ABSTRACT

A solidification matrix includes methacrylate, sodium carbonate, and water. The methacrylate, sodium carbonate, and water interact to form a hydrate solid having a growth exponent of less than about 3%.

13 Claims, No Drawings

SOLIDIFICATION MATRIX

CROSS-REFERENCE TO RELATED APPLICATIONS

This application is a continuation-in-part of U.S. patent application Ser. No. 11/800,286, filed May 4, 2007, which is incorporated herein by reference.

BACKGROUND

The present invention relates generally to the field of solidification and binding agents. In particular, the present invention relates to a methacrylate solidification and binding agent.

The use of solidification technology and solid block detergents in institutional and industrial operations was pioneered in the SOLID POWER® brand technology claimed in Fernholz et al., U.S. Reissue Pat. Nos. 32,762 and 32,818. Additionally, sodium carbonate hydrate cast solid products using substantially hydrated sodium carbonate materials was disclosed in Heile et al., U.S. Pat. Nos. 4,595,520 and 4,680,134.

In more recent years, attention has been directed to producing highly effective detergent materials from less caustic materials such as soda ash, also known as sodium carbonate. Early work in developing the sodium carbonate based detergents found that sodium carbonate hydrate-based materials often swelled, (i.e., were dimensionally unstable) after solidification. Such swelling can interfere with packaging, dispensing, and use. The dimensional instability of the solid materials relates to the unstable nature of various hydrate forms prepared in manufacturing the sodium carbonate solid materials. Early products made with hydrated sodium carbonate typically comprised of anhydrous, a one mole hydrate, a seven mole hydrate, a ten mole hydrate or more mixtures thereof. However, after the product had been manufactured and stored at ambient temperatures, the hydration state of the initial product was found to shift between hydrate forms, e.g., one, seven, and ten mole hydrates, resulting in dimensional instability of the block chemicals. In these conventional solid form compositions, changes in water content and temperature lead to structural and dimensional change, which may lead to a failure of the solid form, resulting in problems such as the inability of the solid form to fit into dispensers for use.

Additionally, conventional solid alkaline detergents, particularly those intended for institutional and commercial use, generally require phosphates in their compositions. The phosphates typically serve multiple purposes in the compositions, for example, to control the rate of solidification, to remove and suspend soils, and as an effective hardness sequestrant. It was found, disclosed, and claimed in U.S. Pat. Nos. 6,258,765, 6,156,715, 6,150,324, and 6,177,392, that a solid block functional material could be made using a binding agent that includes a carbonate salt, an organic acetate, such as an aminocarboxylate, or phosphonate component and water. Due to ecological concerns, further work has recently been directed to replacing phosphorous-containing compounds in detergents. In addition, nitrilotriacetic acid (NTA)-containing aminocarboxylate components used in place of phosphorous-containing compounds in some instances as a binding agents and hardness sequestrants, are believed to be carcinogenic. As such, their use has also been curtailed.

There is an ongoing need to provide alternative solidification technologies which are phosphorous-free and/or NTA-free. However, the lack of predictability in the solidification process and the lack of predictability of dimensional stability in solid form compositions have hampered efforts to successfully replace phosphorous and/or NTA-containing components with environmentally-friendly substitutes.

SUMMARY

A solidification matrix includes methacrylate, sodium carbonate, and water. The methacrylate, sodium carbonate, and water interact to form a hydrate solid having a growth exponent of less than about 3%. The solidification system may be used, for example, in a solid detergent composition.

DETAILED DESCRIPTION

The solidification matrix of the present invention may be employed in any of a wide variety of situations in which a dimensionally stable solid block is desired. The solidification matrix is dimensionally stable and has an appropriate rate of solidification. In addition, the solidification matrix may be substantially free of phosphorous and NTA, making the solidification matrix particularly useful in cleaning applications where it is desired to use an environmentally friendly detergent. Such applications include, but are not limited to: machine and manual warewashing, presoaks, laundry and textile cleaning and destaining, carpet cleaning and destaining, vehicle cleaning and care applications, surface cleaning and destaining, kitchen and bath cleaning and destaining, floor cleaning and destaining, cleaning in place operations, general purpose cleaning and destaining, industrial or household cleaners, and pest control agents. Methods suitable for preparing a solid detergent composition using the solidification matrix are also provided.

The solidification matrix, or binding agent, generally includes methacrylate, sodium carbonate (soda ash), and water for forming solid compositions. Suitable component concentrations for the solidification matrix range from between approximately 1% and approximately 10% by weight methacrylate, between approximately 5% and approximately 40% by weight water, and between approximately 15% and approximately 80% by weight sodium carbonate. Particularly suitable component concentrations for the solidification matrix range from between approximately 1% and approximately 7% methacrylate, between approximately 5% and approximately 10% by weight water, and between approximately 20% and approximately 70% by weight sodium carbonate. Those skilled in the art will appreciate other suitable component concentration ranges for obtaining comparable properties of the solidification matrix.

The actual solidification mechanism of the solidification matrix occurs through ash hydration, or the interaction of the sodium carbonate with water. The methacrylate functions to control the kinetics and thermodynamics of the solidification process and provides a solid binding agent in which additional functional materials may be bound to form a functional solid composition. The methacrylate stabilizes the carbonate hydrates and the functional solid composition by acting as a donor and/or acceptor of free water. By controlling the rate of water migration for hydration of the ash, the methacrylate controls the rate of solidification to provide process and dimensional stability to the resulting product. The rate of solidification is significant because if the solidification matrix solidifies too quickly, the composition may solidify during mixing and stop processing. If the solidification matrix solidifies too slowly, valuable process time is lost. The methacrylate also provides dimensional stability to the end product by ensuring that the solid block does not swell. If the solid block swells after solidification, various problems may occur, including but not limited to: decreased density, integrity, and appearance; and inability to dispense or package the solid block. Generally, a solid product is considered to have dimensional stability if the solid product has a growth exponent of less than about 3% and particularly less than about 2%.

The methacrylate is combined with water prior to incorporation into the detergent composition and can be provided as a solid hydrate or as solid methacrylate that is solvated in an aqueous solution, e.g., in a liquid premix. However, the methacrylate must be in a water matrix when added to the detergent composition for the detergent composition to effectively solidify. In general, an effective amount of methacrylate is considered an amount that effectively controls the kinetics and thermodynamics of the solidification system by controlling the rate and movement of water. An example of a suitable methacrylate includes, but is not limited to, a polymethacrylate. Examples of particularly suitable polymethacrylates include, but are not limited to: sodium polymethacrylate; lithium polymethacrylate; potassium polymethacrylate; ammonium polymethacrylate; and alkanolamine polymethacrylates such as triethanolamine polymethacrylate and monoethanolamine polymethacrylate. An example of a suitable commercially available sodium polymethacrylate includes, but is not limited to, Alcosperse 125, available from ALCO Chemical, Chattanooga, Tenn.

Water may be independently added to the solidification matrix or may be provided in the solidification matrix as a result of its presence in an aqueous material that is added to the detergent composition. For example, materials added to the detergent composition may include water or may be prepared in an aqueous premix available for reaction with the solidification matrix component(s). Typically, water is introduced into the solidification matrix to provide the solidification matrix with a desired viscosity for processing prior to solidification and to provide a desired rate of solidification. The water may also be present as a processing aid and may be removed or become water of hydration. The water may thus be present in the form of aqueous solutions of the binding agent, or aqueous solutions of any of the other ingredients, and/or added aqueous medium as an aid in processing. In addition, it is expected that the aqueous medium may help in the solidification process when is desired to form the concentrate as a solid. It should be additionally appreciated that the water may be provided as deionized water or as softened water.

The amount of water in the resulting solid detergent composition will depend on whether the detergent composition is processed through forming techniques or casting (solidification occurring within a container) techniques. In general, when the components are processed by forming techniques, it is believed that the detergent composition can include a relatively smaller amount of water for solidification compared with the casting techniques. When preparing the solid detergent composition by forming techniques, water may be present in ranges of between about 5% and about 18% by weight, preferably between about 7% and about 15% by weight, and more preferably between about 8% and about 14% by weight. When preparing the solid detergent composition by casting, water may be present in the ranges of between about 19% and about 50% by weight preferably between about 20% and about 40% by weight, and more preferably between about 22% and about 30% by weight.

In an attempt to be "green" and environmentally friendly, the solidification matrix and resulting solid detergent composition may also exclude phosphorus or nitrilotriacetic acid (NTA) containing compounds, making the detergent composition less toxic and more environmentally acceptable. The solidification matrix and resulting solid detergent composition is also a chlorine-compatible binding agent. Phosphorus-free refers to a composition, mixture, or ingredients to which phosphorus-containing compounds are not added. Should phosphorus-containing compounds be present through contamination of a phosphorus-free composition, mixture, or ingredient, the level of phosphorus-containing compounds in the resulting composition is less than approximately 0.5 wt %, less than approximately 0.1 wt %, and often less than approximately 0.01 wt %. NTA-free refers to a composition, mixture, or ingredients to which NTA-containing compounds are not added. Should NTA-containing compounds be present through contamination of an NTA-free composition, mixture, or ingredient, the level of NTA in the resulting composition shall be less than approximately 0.5 wt %, less than approximately 0.1 wt %, and often less than approximately 0.01 wt %.

Additional Functional Materials

The hydrated solidification matrix, or binding agent, can be used to form a solid detergent composition including additional components or agents, such as additional functional materials. As such, in some embodiments, the solidification matrix including sodium carbonate, water, and methacrylate may provide a large amount, or even all of the total weight of the detergent composition, for example, in embodiments having few or no additional functional materials disposed therein. The functional materials provide desired properties and functionalities to the solid detergent composition. For the purpose of this application, the term "functional materials" include a material that when dispersed or dissolved in a use and/or concentrate solution, such as an aqueous solution, provides a beneficial property in a particular use. Some particular examples of functional materials are discussed in more detail below, but it should be understood by those of skill in the art and others that the particular materials discussed are given by way of example only, and that a broad variety of other functional materials may be used. For example, many of the functional materials discussed below relate to materials used in cleaning and/or destaining applications, but it should be understood that other embodiments may include functional materials for use in other applications.

Cleaning Agents

The cleaning agent may include any component that provides soil removal properties when dispersed or dissolved in an aqueous solution and applied to a substrate for removal of soil from the substrate. The cleaning agent typically includes a source of alkalinity and at least one surfactant. In certain embodiments, the cleaning agent preferably includes a surfactant or surfactant system, a source of alkalinity, a water conditioning agent, and an enzyme. The term "surfactant system" refers to a mixture of at least two surfactants, described in more detail below. In certain embodiments, the solidification agent includes sodium hydroxide, sodium carbonate or ash, and sodium metasilicate, or combinations thereof. Thus, the solidification agent may be inorganic in nature and optionally act as a source of alkalinity.

Alkaline Source

The solid detergent composition can include an effective amount of one or more alkaline sources to enhance cleaning of a substrate and improve soil removal performance of the detergent composition. In general, it is expected that the concentrate will include the alkaline source in an amount of at least about 5% by weight, at least about 10% by weight, or at least about 15% by weight. In order to provide sufficient room for other components in the concentrate, the alkaline source can be provided in the concentrate in an amount of less than about 75% by weight, less than about 60% by weight, less than about 40% by weight, less than about 30% by weight, or less than about 20% by weight. The alkalinity source may constitute between about 0.1% and about 90% by weight, between about 0.5% and about 80% by weight, and between about 1% and about 60% by weight of the total weight of the solid detergent composition.

An effective amount of one or more alkaline sources should be considered as an amount that provides a use composition having a pH of at least about 8. When the use composition has a pH of between about 8 and about 10, it can be considered mildly alkaline, and when the pH is greater than about 12, the use composition can be considered caustic. In general, it is desirable to provide the use composition as a mildly alkaline cleaning composition because it is considered to be safer than the caustic based use compositions. In some circumstances, the solid detergent composition may provide a use composition that is useful at pH levels below about 8. In such compositions, the alkaline source may be omitted, and additional pH adjusting agents may be used to provide the use composition with the desired pH. Accordingly, it should be understood that the source of alkalinity is as an optional component to the solid detergent composition.

Examples of suitable alkaline sources of the solid detergent composition include, but are not limited to: an alkali metal carbonate and an alkali metal hydroxide. Exemplary alkali metal carbonates that can be used include, but are not limited to: sodium or potassium carbonate, bicarbonate, sesquicarbonate, and mixtures thereof. Exemplary alkali metal hydroxides that can be used include, but are not limited to: sodium or potassium hydroxide. The alkali metal hydroxide may be added to the composition in any form known in the art, including as solid beads, dissolved in an aqueous solution, or a combination thereof. Alkali metal hydroxides are commercially available as a solid in the form of prilled solids or beads having a mix of particle sizes ranging from about 12-100 U.S. mesh, or as an aqueous solution, as for example, as a 50% and a 73% by weight solution. It is preferred that the alkali metal hydroxide is added in the form of an aqueous solution, preferably a 50% by weight hydroxide solution, to reduce the amount of heat generated in the composition due to hydration of the solid alkali material.

In addition to the first alkalinity source, the solid detergent composition may comprise a secondary alkalinity source. Examples of useful secondary alkaline sources include, but are not limited to: metal silicates such as sodium or potassium silicate or metasilicate; metal carbonates such as sodium or potassium carbonate, bicarbonate, sesquicarbonate; metal borates such as sodium or potassium borate; and ethanolamines and amines. Such alkalinity agents are commonly available in either aqueous or powdered form, either of which is useful in formulating the present solid detergent compositions.

Surfactants

The solid detergent composition can include at least one cleaning agent comprising a surfactant or surfactant system. A variety of surfactants can be used in a solid detergent composition, including, but not limited to: anionic, nonionic, cationic, and zwitterionic surfactants. It should be understood that surfactants are an optional component of the solid detergent composition and can be excluded from the concentrate. Exemplary surfactants that can be used are commercially available from a number of sources. For a discussion of surfactants, see Kirk-Othmer, Encyclopedia of Chemical Technology, Third Edition, volume 8, pages 900-912. When the solid detergent composition includes a cleaning agent, the cleaning agent is provided in an amount effective to provide a desired level of cleaning. The solid detergent composition, when provided as a concentrate, can include the cleaning agent in a range of about 0.05% to about 20% by weight, about 0.5% to about 15% by weight, about 1% to about 15% by weight, about 1.5% to about 10% by weight, and about 2% to about 5% by weight. Additional exemplary ranges of surfactant in a concentrate include about 0.5% to about 5% by weight, and about 1% to about 3% by weight.

Examples of anionic surfactants useful in the solid detergent composition include, but are not limited to: carboxylates such as alkylcarboxylates (carboxylic acid salts) and polyalkoxycarboxylates, alcohol ethoxylate carboxylates, nonylphenol ethoxylate carboxylates; sulfonates such as alkylsulfonates, alkylbenzenesulfonates, alkylarylsulfonates, sulfonated fatty acid esters; sulfates such as sulfated alcohols, sulfated alcohol ethoxylates, sulfated alkylphenols, alkylsulfates, sulfosuccinates, and alkylether sulfates. Exemplary anionic surfactants include, but are not limited to: sodium alkylarylsulfonate, alpha-olefinsulfonate, and fatty alcohol sulfates.

Examples of nonionic surfactants useful in the solid detergent composition include, but are not limited to, those having a polyalkylene oxide polymer as a portion of the surfactant molecule. Such nonionic surfactants include, but are not limited to: chlorine-, benzyl-, methyl-, ethyl-, propyl-, butyl- and other like alkyl-capped polyethylene glycol ethers of fatty alcohols; polyalkylene oxide free nonionics such as alkyl polyglycosides; sorbitan and sucrose esters and their ethoxylates; alkoxylated amines such as alkoxylated ethylene diamine; alcohol alkoxylates such as alcohol ethoxylate propoxylates, alcohol propoxylates, alcohol propoxylate ethoxylate propoxylates, alcohol ethoxylate butoxylates; nonylphenol ethoxylate, polyoxyethylene glycol ether; carboxylic acid esters such as glycerol esters, polyoxyethylene esters, ethoxylated and glycol esters of fatty acids; carboxylic amides such as diethanolamine condensates, monoalkanolamine condensates, polyoxyethylene fatty acid amides; and polyalkylene oxide block copolymers. An example of a commercially available ethylene oxide/propylene oxide block copolymer includes, but is not limited to, PLURONIC®, available from BASF Corporation, Florham Park, N.J. An example of a commercially available silicone surfactant includes, but is not limited to, ABIL® B8852, available from Goldschmidt Chemical Corporation, Hopewell, Va.

Examples of cationic surfactants that can be used in the solid detergent composition include, but are not limited to: amines such as primary, secondary and tertiary monoamines with $C_{18}$ alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like; and quaternary ammonium salts, as for example, alkylquatemary ammonium chloride surfactants such as n-alkyl($C_{12}$-$C_{18}$)dimethylbenzyl ammonium chloride, n-tetradecyldimethylbenzylammonium chloride monohydrate, and a naphthylene-substituted quaternary ammonium chloride such as dimethyl-1-naphthylmethylammonium chloride. The cationic surfactant can be used to provide sanitizing properties.

Examples of zwitterionic surfactants that can be used in the solid detergent composition include, but are not limited to: betaines, imidazolines, and propionates.

Because the solid detergent composition is intended to be used in an automatic dishwashing or warewashing machine, the surfactants selected, if any surfactant is used, can be those that provide an acceptable level of foaming when used inside a dishwashing or warewashing machine. It should be understood that solid detergent compositions for use in automatic dishwashing or warewashing machines are generally considered to be low-foaming compositions. One would understand that low foaming surfactants that provide the desired level of detersive activity are advantageous in an environment such as a dishwashing machine where the presence of large amounts of foaming can be problematic. In addition to selecting low foaming surfactants, one would understand that defoaming agents can be utilized to reduce the generation of foam. Accordingly, surfactants that are considered low foaming surfactants can be used. In addition, other surfactants can be used in conjunction with a defoaming agent to control the level of foaming.

Some surfactants can also function as secondary solidifying agents. For example, anionic surfactants which have high melting points provide a solid at the temperature of application. Anionic surfactants which have been found most useful include, but are not limited to: linear alkyl benzene sulfonate surfactants, alcohol sulfates, alcohol ether sulfates, and alpha olefin sulfonates. Generally, linear alkyl benzene sulfonates are preferred for reasons of cost and efficiency. Amphoteric or zwitterionic surfactants are also useful in providing detergency, emulsification, wetting and conditioning properties. Representative amphoteric surfactants include, but are not limited to: N-coco-3-aminopropionic acid and acid salts, N-tallow-3-iminodiproprionate salts, N-lauryl-3-iminodiproprionate disodium salt, N-carboxymethyl-N-cocoalkyl-N-dimethylammonium hydroxide, N-carboxymethyl-N-dimethyl-N-(9-octadecenyl)ammonium hydroxide, (1-carboxyheptadecyl)trimethylammonium hydroxide, (1-carboxyundecyl)trimethylammonium hydroxide, N-cocoamidoethyl-N-hydroxyethylglycine sodium salt, N-hydroxyethyl-N-stearamidoglycine sodium salt, N-hydroxyethyl-N-lauramido-.beta.-alanine sodium salt, N-cocoamido-N-hydroxyethyl-.beta.-alanine sodium salt, mixed alcyclic amines and their ethoxylated and sulfated sodium salts, 2-alkyl-1-carboxymethyl-1-hydroxyethyl-2-imidazolinium hydroxide sodium salt or free acid wherein the alkyl group may be nonyl, undecyl, and heptadecyl. Other useful amphoteric surfactants include, but are not limited to: 1,1-bis(carboxymethyl)-2-undecyl-2-imidazolinium hydroxide disodium salt and oleic acid-ethylenediamine condensate, propoxylated and sulfated sodium salt, and amine oxide amphoteric surfactants.

Secondary Solidification Agents

In some embodiments, the compositions can include a secondary solidification agent. For example, the solidification agent may be inorganic in nature and may also act optionally as a source of alkalinity. In certain embodiments, the secondary solidification agent includes sodium hydroxide, sodium carbonate or ash, and sodium metasilicate, or combinations thereof.

Suitable secondary solidifying agents include, but are not limited to: alkali metal hydroxides, alkali metal phosphates, anhydrous sodium carbonate, anhydrous sodium sulfate, anhydrous sodium acetate, and other known hydratable compounds. The amount of secondary solidifying agent necessary to achieve solidification depends upon several factors, including the exact solidifying agent employed, the amount of water in the composition, and the hydration capacity of the other detergent components. In certain embodiments, the secondary solidifying agent may also serve as an alkaline source.

In some embodiments, solid detergent compositions including a substantial portion of sodium hydroxide are cast and solidified. For example, sodium hydroxide hydrate can be used to solidify a cast material in a freezing process using the low melting point of sodium hydroxide monohydrate (about 50° C.-65° C.). The active components of the detergent were mixed with the molten sodium hydroxide and cooled to solidify. The resulting solid was a matrix of hydrated solid sodium hydroxide with the detergent ingredients dissolved or suspended in the hydrated matrix. In conventionally cast solid and other prior art hydrated solids, the hydrated chemicals are reacted with water and the hydration reaction is run to substantial completion. The sodium hydroxide also provided substantial cleaning in warewashing systems and in other use loci that require rapid and complete soil removal. In these early products, sodium hydroxide was an ideal candidate because the highly alkaline nature of the caustic material provided excellent cleaning. Cast solids may also be formed using a combination of sodium hydroxide and sodium carbonate. Certain embodiments contain at least about 30 wt. % of an alkali metal hydroxide in combination with water of hydration. Other embodiments contain about 30 wt. % to about 50 wt. % of an alkali metal hydroxide.

In other embodiments, the secondary solidification agent of the solid detergent composition includes alkaline carbonate, water, and a sequestering agent. For example, the composition may include an alkali metal salt of an organophosphonate at about 1 wt. % to about 30 wt. %, preferably about 3 wt. % to about 15 wt. % of a potassium salt; and water at about 5 wt. % to about 15 wt. %, preferably about 5 wt. % to about 12 wt. %; and alkali metal carbonate at about 25 wt. % to about 80 wt. %, preferably about 30 wt. % to about 55 wt. %. A single E-form hydrate binder composition forms as this material solidifies. E-form materials are described in U.S. Pat. Nos. 6,177,392, 6,660,707, 6,156,715, 6,410,495, 6,653,266, 6,831,054, and 6,583,094, all of which are incorporated herein by reference.

The solid detergent composition may comprise a major proportion of carbonate monohydrate, a portion of non-hydrated (substantially anhydrous) alkali metal carbonate and the E-form binder composition comprising a fraction of the carbonate material, an amount of the organophosphonate and water of hydration.

In yet other embodiments, the secondary solidification agent includes an effective amount of one or more anhydrous salts which are selected to hydrate and melt at a temperature below that at which significant phosphate reversion occurs. Such temperatures typically fall within the range of about 20° C. to about 80° C., preferably about 33° C. to about 65° C., and more preferably salts which melt at about 35° C. to about 50° C. will be used. The dispersed, hydrated salt solidifies when the emulsion is cooled and can bind sufficient free water to afford a stable, homogeneous solid at ambient temperatures, e.g., at about 15° C., to about 25° C. Preferably an amount of anhydrous sodium carbonate, anhydrous sodium sulfate or mixtures thereof effective to solidify the composition when they are cooled to ambient temperatures will be employed. The amount of secondary solidifying agent is related to the percent of water present in the composition as well as the hydration capacity of the other detergent components.

Builders or Water Conditioners

The solid detergent composition can include one or more building agents, also called chelating or sequestering agents (e.g., builders), including, but not limited to: a condensed phosphate, a phosphonate, an aminocarboxylic acid, or a polyacrylate. In general, a chelating agent is a molecule capable of coordinating (i.e., binding) the metal ions commonly found in natural water to prevent the metal ions from interfering with the action of the other detersive ingredients of a cleaning composition. The chelating/sequestering agent may also function as a threshold agent when included in an effective amount. Other sequestrants are useful for only sequestering properties. Preferable levels of addition for builders that can also be chelating or sequestering agents are between about 0.1% to about 70% by weight, about 1% to about 60% by weight, or about 1.5% to about 50% by weight. If the solid detergent is provided as a concentrate, the concentrate can include between approximately 1% to approximately 60% by weight, between approximately 3% to approximately 50% by weight, and between approximately 6% to approximately 45% by weight of the builders. Additional ranges of the builders include between approximately 3% to approximately 20% by weight, between approximately 6% to approximately 15% by weight, between approximately 25% to approximately 50% by weight, and between approximately 35% to approximately 45% by weight.

Examples of condensed phosphates include, but are not limited to: sodium and potassium orthophosphate, sodium and potassium pyrophosphate, sodium tripolyphosphate, and sodium hexametaphosphate. A condensed phosphate may also assist, to a limited extent, in solidification of the solid detergent composition by fixing the free water present in the composition as water of hydration.

Examples of phosphonates included, but are not limited to: 1-hydroxyethane-1,1-diphosphonic acid, $CH_2C(OH)[PO(OH)_2]_2$; aminotri(methylenephosphonic acid), $N[CH_2PO(OH)_2]_3$; aminotri(methylenephosphonate), sodium salt (ATMP), $N[CH_2PO(ONa)_2]_3$; 2-hydroxyethyliminobis(methylenephosphonic acid), $HOCH_2CH_2N[CH_2PO(OH)_2]_2$; diethylenetriaminepenta(methylenephosphonic acid), $(HO)_2POCH_2N[CH_2CH_2N[CH_2PO(OH)_2]_2]_2$; diethylenetriaminepenta(methylenephosphonate), sodium salt (DTPMP), $C_9H_{(28-x)}N_3Na_xO_{15}P_5$ (x=7); hexamethylenediamine(tetramethylenephosphonate), potassium salt, $C_{10}H_{(28-x)}N_2K_xO_{12}P_4$ (x=6); bis(hexamethylene)triamine(pentamethylenephosphonic acid), $(HO_2)POCH_2N[(CH_2)_2N[CH_2PO(OH)_2]_2]_2$; and phosphorus acid, $H_3PO_3$. A preferred phosphonate combination is ATMP and DTPMP. A neutralized or alkaline phosphonate, or a combination of the phosphonate with an alkali source prior to being added into the mixture such that there is little or no heat or gas generated by a neutralization reaction when the phosphonate is added is preferred.

The solid detergent compositions can contain a non-phosphorus based builder. It should be understood that various components may include trace amounts of phosphorous. However, a composition that is free of phosphorous does not include phosphate or phosphonate builder or chelating components as an intentionally added component. Carboxylates such as citrate or gluconate are suitable. Useful aminocarboxylic acid materials containing little or no NTA include, but are not limited to: N-hydroxyethylaminodiacetic acid, ethylenediaminetetraacetic acid (EDTA), hydroxyethylenediaminetetraacetic acid, diethylenetriaminepentaacetic acid, N-hydroxyethyl-ethylenediaminetriacetic acid (HEDTA), diethylenetriaminepentaacetic acid (DTPA), and other similar acids having an amino group with a carboxylic acid substituent.

Water conditioning polymers can be used as non-phosphorus containing builders. Exemplary water conditioning polymers include, but are not limited to: polycarboxylates. Exemplary polycarboxylates that can be used as builders and/or water conditioning polymers include, but are not limited to: those having pendant carboxylate ($—CO_2^-$) groups such as polyacrylic acid, maleic, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, and hydrolyzed acrylonitrile-methacrylonitrile copolymers. For a further discussion of chelating agents/sequestrants, see Kirk-Othmer, Encyclopedia of Chemical Technology, Third Edition, volume 5, pages 339-366 and volume 23, pages 319-320, the disclosure of which is incorporated by reference herein.

Hardening Agents

The solid detergent compositions can also include a hardening agent in addition to, or in the form of, the builder. A hardening agent is a compound or system of compounds, organic or inorganic, which significantly contributes to the uniform solidification of the composition. Preferably, the hardening agents are compatible with the cleaning agent and other active ingredients of the composition and are capable of providing an effective amount of hardness and/or aqueous solubility to the processed composition. The hardening agents should also be capable of forming a homogeneous matrix with the cleaning agent and other ingredients when mixed and solidified to provide a uniform dissolution of the cleaning agent from the solid detergent composition during use.

The amount of hardening agent included in the solid detergent composition will vary according to factors including, but not limited to: the type of solid detergent composition being prepared, the ingredients of the solid detergent composition, the intended use of the composition, the quantity of dispensing solution applied to the solid composition over time during use, the temperature of the dispensing solution, the hardness of the dispensing solution, the physical size of the solid detergent composition, the concentration of the other ingredients, and the concentration of the cleaning agent in the composition. It is preferred that the amount of the hardening agent included in the solid detergent composition is effective to combine with the cleaning agent and other ingredients of the composition to form a homogeneous mixture under continuous mixing conditions and a temperature at or below the melting temperature of the hardening agent.

It is also preferred that the hardening agent form a matrix with the cleaning agent and other ingredients which will harden to a solid form under ambient temperatures of approximately 30° C. to approximately 50° C., preferably approximately 35° C. to approximately 45° C., after mixing ceases and the mixture is dispensed from the mixing system, within approximately 1 minute to approximately 3 hours, preferably approximately 2 minutes to approximately 2 hours, and preferably approximately 5 minutes to approximately 1 hour. A minimal amount of heat from an external source may be applied to the mixture to facilitate processing of the mixture. It is preferred that the amount of the hardening agent included in the solid detergent composition is effective to provide a desired hardness and desired rate of controlled solubility of the processed composition when placed in an aqueous medium to achieve a desired rate of dispensing the cleaning agent from the solidified composition during use.

The hardening agent may be an organic or an inorganic hardening agent. A preferred organic hardening agent is a polyethylene glycol (PEG) compound. The solidification rate of solid detergent compositions comprising a polyethylene glycol hardening agent will vary, at least in part, according to the amount and the molecular weight of the polyethylene glycol added to the composition. Examples of suitable polyethylene glycols include, but are not limited to: solid polyethylene glycols of the general formula $H(OCH_2CH_2)_nOH$, where n is greater than 15, more preferably approximately 30 to approximately 1700. Typically, the polyethylene glycol is a solid in the form of a free-flowing powder or flakes, having a molecular weight of approximately 1,000 to approximately 100,000, preferably having a molecular weight of at least approximately 1,450 to approximately 20,000, more preferably between approximately 1,450 to approximately 8,000. The polyethylene glycol is present at a concentration of from approximately 1% to 75% by weight and preferably approximately 3% to approximately 15% by weight. Suitable polyethylene glycol compounds include, but are not limited to: PEG 4000, PEG 1450, and PEG 8000 among others, with PEG 4000 and PEG 8000 being most preferred. An example of a commercially available solid polyethylene glycol includes, but is not limited to: CARBOWAX, available from Union Carbide Corporation, Houston, Tex.

Preferred inorganic hardening agents are hydratable inorganic salts, including, but not limited to: sulfates, acetates, and bicarbonates. The inorganic hardening agents are present at concentrations of up to approximately 50% by weight, preferably approximately 5% to approximately 25% by weight, and more preferably approximately 5% to approximately 15% by weight.

Urea particles can also be employed as hardeners in the solid detergent compositions. The solidification rate of the compositions will vary, at least in part, to factors including, but not limited to: the amount, the particle size, and the shape of the urea added to the composition. For example, a particulate form of urea can be combined with a cleaning agent and other ingredients, and preferably a minor but effective amount of water. The amount and particle size of the urea is effective to combine with the cleaning agent and other ingredients to form a homogeneous mixture without the application of heat from an external source to melt the urea and other ingredients to a molten stage. It is preferred that the amount of urea included in the solid detergent composition is effective to provide a desired hardness and desired rate of solubility of the composition when placed in an aqueous medium to achieve a desired rate of dispensing the cleaning agent from the solidified composition during use. Preferably, the composition includes between approximately 5% to approximately 90% by weight urea, preferably between approximately 8% and approximately 40% by weight urea, and more preferably between approximately 10% and approximately 30% by weight urea.

The urea may be in the form of prilled beads or powder. Prilled urea is generally available from commercial sources as a mixture of particle sizes ranging from about 8-15 U.S. mesh, as for example, from Arcadian Sohio Company, Nitrogen Chemicals Division. A prilled form of urea is preferably milled to reduce the particle size to about 50 U.S. mesh to about 125 U.S. mesh, preferably about 75-100 U.S. mesh, preferably using a wet mill such as a single or twin-screw extruder, a Teledyne mixer, a Ross emulsifier, and the like.

Bleaching Agents

Bleaching agents suitable for use in the solid detergent composition for lightening or whitening a substrate include bleaching compounds capable of liberating an active halogen species, such as $Cl_2$, $Br_2$, $—OCl^-$ and/or $—OBr^-$, under conditions typically encountered during the cleansing process. Suitable bleaching agents for use in the solid detergent compositions include, but are not limited to: chlorine-containing compounds such as chlorines, hypochlorites, or chloramines. Exemplary halogen-releasing compounds include, but are not limited to: the alkali metal dichloroisocyanurates, chlorinated trisodium phosphate, the alkali metal hypochlorites, monochloramine, and dichloramine. Encapsulated chlorine sources may also be used to enhance the stability of the chlorine source in the composition (see, for example, U.S. Pat. Nos. 4,618,914 and 4,830,773, the disclosure of which is incorporated by reference herein). A bleaching agent may also be a peroxygen or active oxygen source such as hydrogen peroxide, perborates, sodium carbonate peroxyhydrate, potassium permonosulfate, and sodium perborate mono and tetrahydrate, with and without activators such as tetraacetylethylene diamine. When the concentrate includes a bleaching agent, it can be included in an amount of between approximately 0.1% and approximately 60% by weight, between approximately 1% and approximately 20% by weight, between approximately 3% and approximately 8% by weight, and between approximately 3% and approximately 6% by weight.

Fillers

The solid detergent composition can include an effective amount of detergent fillers which do not perform as a cleaning agent per se, but cooperates with the cleaning agent to enhance the overall cleaning capacity of the composition. Examples of detergent fillers suitable for use in the present cleaning compositions include, but are not limited to: sodium sulfate, sodium chloride, starch, and sugars. When the concentrate includes a detergent filler, it can be included in an amount up to approximately 50% by weight, between approximately 1% and approximately 30% by weight, or between approximately 1.5% and approximately 25% by weight.

Defoaming Agents

A defoaming agent for reducing the stability of foam may also be included in the warewashing composition. Examples of defoaming agents include, but are not limited to: ethylene oxide/propylene block copolymers such as those available under the name Pluronic N-3; silicone compounds such as silica dispersed in polydimethylsitoxane, polydimethylsiloxane, and functionalized polydimethylsiloxane such as those available under the name Abil B9952; fatty amides, hydrocarbon waxes, fatty acids, fatty esters, fatty alcohols, fatty acid soaps, ethoxylates, mineral oils, polyethylene glycol esters, and alkyl phosphate esters such as monostearyl phosphate. A discussion of defoaming agents may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated herein by reference. When the concentrate includes a defoaming agent, the defoaming agent can be provided in an amount of between approximately 0.0001% and approximately 10% by weight, between approximately 0.001% and approximately 5% by weight, or between approximately 0.01% and approximately 1.0% by weight.

Anti-Redeposition Agents

The solid detergent composition can include an anti-redeposition agent for facilitating sustained suspension of soils in a cleaning solution and preventing the removed soils from being redeposited onto the substrate being cleaned. Examples of suitable anti-redeposition agents include, but are not limited to: polyacrylates, styrene maleic anhydride copolymers, cellulosic derivatives such as hydroxyethyl cellulose, and hydroxypropyl cellulose. When the concentrate includes an anti-redeposition agent, the anti-redeposition agent can be included in an amount of between approximately 0.5% and approximately 10% by weight, and between approximately 1% and approximately 5% by weight.

Stabilizing Agents

The solid detergent composition may also include stabilizing agents. Examples of suitable stabilizing agents include, but are not limited to: borate, calcium/magnesium ions, propylene glycol, and mixtures thereof. The concentrate need not include a stabilizing agent, but when the concentrate includes a stabilizing agent, it can be included in an amount that provides the desired level of stability of the concentrate. Exemplary ranges of the stabilizing agent include up to approximately 20% by weight, between approximately 0.5% and approximately 15% by weight, and between approximately 2% and approximately 10% by weight.

Dispersants

The solid detergent composition may also include dispersants. Examples of suitable dispersants that can be used in the solid detergent composition include, but are not limited to: maleic acid/olefin copolymers, polyacrylic acid, and mixtures thereof. The concentrate need not include a dispersant, but when a dispersant is included it can be included in an amount that provides the desired dispersant properties. Exemplary ranges of the dispersant in the concentrate can be up to approximately 20% by weight, between approximately 0.5% and approximately 15% by weight, and between approximately 2% and approximately 9% by weight.

Enzymes

Enzymes that can be included in the solid detergent composition include those enzymes that aid in the removal of starch and/or protein stains. Exemplary types of enzymes include, but are not limited to: proteases, alpha-amylases, and mixtures thereof. Exemplary proteases that can be used include, but are not limited to: those derived from *Bacillus licheniformix, Bacillus lenus, Bacillus alcalophilus*, and *Bacillus amyloliquefacins*. Exemplary alpha-amylases include *Bacillus subtilis, Bacillus amyloliquefaceins* and *Bacillus licheniformis*. The concentrate need not include an enzyme, but when the concentrate includes an enzyme, it can be included in an amount that provides the desired enzymatic activity when the solid detergent composition is provided as a use composition. Exemplary ranges of the enzyme in the concentrate include up to approximately 15% by weight, between approximately 0.5% to approximately 10% by weight, and between approximately 1% to approximately 5% by weight.

Glass and Metal Corrosion Inhibitors

The solid detergent composition can include a metal corrosion inhibitor in an amount up to approximately 50% by weight, between approximately 1% and approximately 40% by weight, or between approximately 3% and approximately 30% by weight. The corrosion inhibitor is included in the solid detergent composition in an amount sufficient to provide a use solution that exhibits a rate of corrosion and/or etching of glass that is less than the rate of corrosion and/or etching of glass for an otherwise identical use solution except for the absence of the corrosion inhibitor. It is expected that the use solution will include at least approximately 6 parts per million (ppm) of the corrosion inhibitor to provide desired corrosion inhibition properties. It is expected that larger amounts of corrosion inhibitor can be used in the use solution without deleterious effects. It is expected that at a certain point, the additive effect of increased corrosion and/or etching resistance with increasing corrosion inhibitor concentration will be lost, and additional corrosion inhibitor will simply increase the cost of using the solid detergent composition. The use solution can include between approximately 6 ppm and approximately 300 ppm of the corrosion inhibitor, and between approximately 20 ppm and approximately 200 ppm of the corrosion inhibitor. Examples of suitable corrosion inhibitors include, but are not limited to: a combination of a source of aluminum ion and a source of zinc ion, as well as an alkaline metal silicate or hydrate thereof.

The corrosion inhibitor can refer to the combination of a source of aluminum ion and a source of zinc ion. The source of aluminum ion and the source of zinc ion provide aluminum ion and zinc ion, respectively, when the solid detergent composition is provided in the form of a use solution. The amount of the corrosion inhibitor is calculated based upon the combined amount of the source of aluminum ion and the source of zinc ion. Anything that provides an aluminum ion in a use solution can be referred to as a source of aluminum ion, and anything that provides a zinc ion when provided in a use solution can be referred to as a source of zinc ion. It is not necessary for the source of aluminum ion and/or the source of zinc ion to react to form the aluminum ion and/or the zinc ion. It should be understood that aluminum ions can be considered a source of aluminum ion, and zinc ions can be considered a source of zinc ion. The source of aluminum ion and the source of zinc ion can be provided as organic salts, inorganic salts, and mixtures thereof. Exemplary sources of aluminum ion include, but are not limited to: aluminum salts such as sodium aluminate, aluminum bromide, aluminum chlorate, aluminum chloride, aluminum iodide, aluminum nitrate, aluminum sulfate, aluminum acetate, aluminum formate, aluminum tartrate, aluminum lactate, aluminum oleate, aluminum bromate, aluminum borate, aluminum potassium sulfate, aluminum zinc sulfate, and aluminum phosphate. Exemplary sources of zinc ion include, but are not limited to: zinc salts such as zinc chloride, zinc sulfate, zinc nitrate, zinc iodide, zinc thiocyanate, zinc fluorosilicate, zinc dichromate, zinc chlorate, sodium zincate, zinc gluconate, zinc acetate, zinc benzoate, zinc citrate, zinc lactate, zinc formate, zinc bromate, zinc bromide, zinc fluoride, zinc fluorosilicate, and zinc salicylate.

The applicants discovered that by controlling the ratio of the aluminum ion to the zinc ion in the use solution, it is possible to provide reduced corrosion and/or etching of glassware and ceramics compared with the use of either component alone. That is, the combination of the aluminum ion and the zinc ion can provide a synergy in the reduction of corrosion and/or etching. The ratio of the source of aluminum ion to the source of zinc ion can be controlled to provide a synergistic effect. In general, the weight ratio of aluminum ion to zinc ion in the use solution can be between at least approximately 6:1, can be less than approximately 1:20, and can be between approximately 2:1 and approximately 1:15.

An effective amount of an alkaline metal silicate or hydrate thereof can be employed in the compositions and processes of the invention to form a stable solid detergent composition having metal protecting capacity. The silicates employed in the compositions of the invention are those that have conventionally been used in solid detergent formulations. For example, typical alkali metal silicates are those powdered, particulate or granular silicates which are either anhydrous or preferably which contain water of hydration (approximately 5% to approximately 25% by weight, preferably approximately 15% to approximately 20% by weight water of hydration). These silicates are preferably sodium silicates and have a $Na_2O:SiO_2$ ratio of approximately 1:1 to approximately 1:5, respectively, and typically contain available water in the amount of from approximately 5% to approximately 25% by weight. In general, the silicates have a $Na_2O:SiO_2$ ratio of approximately 1:1 to approximately 1:3.75, preferably approximately 1:1.5 to approximately 1:3.75 and most preferably approximately 1:1.5 to approximately 1:2.5. A silicate with a $Na_2O:SiO_2$ ratio of approximately 1:2 and approximately 16% to approximately 22% by weight water of hydration, is most preferred. For example, such silicates are available in powder form as GD Silicate and in granular form as Britesil H-20, available from PQ Corporation, Valley Forge, Pa. These ratios may be obtained with single silicate compositions or combinations of silicates which upon combination result in the preferred ratio. The hydrated silicates at preferred ratios, a $Na_2O:SiO_2$ ratio of approximately 1:1.5 to approximately 1:2.5, have been found to provide the optimum metal protection and rapidly forming solid block detergent. Hydrated silicates are preferred.

Silicates can be included in the solid detergent composition to provide for metal protection but are additionally known to provide alkalinity and additionally function as anti-redeposition agents. Exemplary silicates include, but are not limited to: sodium silicate and potassium silicate. The solid detergent composition can be provided without silicates, but when silicates are included, they can be included in amounts that provide for desired metal protection. The concentrate can include silicates in amounts of at least approximately 1% by weight, at least approximately 5% by weight, at least approximately 10% by weight, and at least approximately 15% by weight. In addition, in order to provide sufficient room for other components in the concentrate, the silicate component can be provided at a level of less than approximately 35% by weight, less than approximately 25% by weight, less than approximately 20% by weight, and less than approximately 15% by weight.

Fragrances and Dyes

Various dyes, odorants including perfumes, and other aesthetic enhancing agents can also be included in the composition. Suitable dyes that may be included to alter the appearance of the composition, include, but are not limited to: Direct Blue 86, available from Mac Dye-Chem Industries, Ahmedabad, India; Fastusol Blue, available from Mobay Chemical Corporation, Pittsburgh, Pa.; Acid Orange 7, available from American Cyanamid Company, Wayne, N.J.; Basic Violet 10 and Sandolan Blue/Acid Blue 182, available from Sandoz, Princeton, N.J.; Acid Yellow 23, available from Chemos GmbH, Regenstauf, Germany; Acid Yellow 17, available from Sigma Chemical, St. Louis, Mo.; Sap Green and Metanil Yellow, available from Keyston Analine and Chemical, Chicago, Ill.; Acid Blue 9, available from Emerald Hilton Davis, LLC, Cincinnati, Ohio; Hisol Fast Red and Fluorescein, available from Capitol Color and Chemical Company, Newark, N.J.; and Acid Green 25, Ciba Specialty Chemicals Corporation, Greenboro, N.C.

Fragrances or perfumes that may be included in the compositions include, but are not limited to: terpenoids such as citronellol, aldehydes such as amyl cinnamaldehyde, a jasmine such as ClS-jasmine or jasmal, and vanillin.

Thickeners

The solid detergent compositions can include a rheology modifier or a thickener. The rheology modifier may provide the following functions: increasing the viscosity of the compositions; increasing the particle size of liquid use solutions when dispensed through a spray nozzle; providing the use solutions with vertical cling to surfaces; providing particle suspension within the use solutions; or reducing the evaporation rate of the use solutions.

The rheology modifier may provide a use composition that is pseudo plastic, in other words the use composition or material when left undisturbed (in a shear mode), retains a high viscosity. However, when sheared, the viscosity of the material is substantially but reversibly reduced. After the shear action is removed, the viscosity returns. These properties permit the application of the material through a spray head. When sprayed through a nozzle, the material undergoes shear as it is drawn up a feed tube into a spray head under the influence of pressure and is sheared by the action of a pump in a pump action sprayer. In either case, the viscosity can drop to a point such that substantial quantities of the material can be applied using the spray devices used to apply the material to a soiled surface. However, once the material comes to rest on a soiled surface, the materials can regain high viscosity to ensure that the material remains in place on the soil. Preferably, the material can be applied to a surface resulting in a substantial coating of the material that provides the cleaning components in sufficient concentration to result in lifting and removal of the hardened or baked-on soil. While in contact with the soil on vertical or inclined surfaces, the thickeners in conjunction with the other components of the cleaner minimize dripping, sagging, slumping or other movement of the material under the effects of gravity. The material should be formulated such that the viscosity of the material is adequate to maintain contact between substantial quantities of the film of the material with the soil for at least a minute, preferably five minutes or more.

Examples of suitable thickeners or rheology modifiers are polymeric thickeners including, but not limited to: polymers or natural polymers or gums derived from plant or animal sources. Such materials may be polysaccharides such as large polysaccharide molecules having substantial thickening capacity. Thickeners or rheology modifiers also include clays.

A substantially soluble polymeric thickener can be used to provide increased viscosity or increased conductivity to the use compositions. Examples of polymeric thickeners for the aqueous compositions of the invention include, but are not limited to: carboxylated vinyl polymers such as polyacrylic acids and sodium salts thereof, ethoxylated cellulose, polyacrylamide thickeners, cross-linked, xanthan compositions, sodium alginate and algin products, hydroxypropyl cellulose, hydroxyethyl cellulose, and other similar aqueous thickeners that have some substantial proportion of water solubility. Examples of suitable commercially available thickeners include, but are not limited to: Acusol, available from Rohm & Haas Company, Philadelphia, Pa.; and Carbopol, available from B.F. Goodrich, Charlotte, N.C.

Examples of suitable polymeric thickeners include, but not limited to: polysaccharides. An example of a suitable commercially available polysaccharide includes, but is not limited to, Diutan, available from Kelco Division of Merck, San Diego, Calif. Thickeners for use in the solid detergent compositions further include polyvinyl alcohol thickeners, such as, fully hydrolyzed (greater than 98.5 mol acetate replaced with the —OH function).

An example of a particularly suitable polysaccharide includes, but is not limited to, xanthans. Such xanthan polymers are preferred due to their high water solubility, and great thickening power. Xanthan is an extracellular polysaccharide of xanthomonas campestras. Xanthan may be made by fermentation based on corn sugar or other corn sweetener by-products. Xanthan comprises a poly beta-(1-4)-D-Glucopyranosyl backbone chain, similar to that found in cellulose. Aqueous dispersions of xanthan gum and its derivatives exhibit novel and remarkable rheological properties. Low concentrations of the gum have relatively high viscosities which permit it to be used economically. Xanthan gum solutions exhibit high pseudo plasticity, i.e. over a wide range of concentrations, rapid shear thinning occurs that is generally understood to be instantaneously reversible. Non-sheared materials have viscosities that appear to be independent of the pH and independent of temperature over wide ranges. Preferred xanthan materials include crosslinked xanthan materials. Xanthan polymers can be crosslinked with a variety of known covalent reacting crosslinking agents reactive with the hydroxyl functionality of large polysaccharide molecules and can also be crosslinked using divalent, trivalent or polyvalent metal ions. Such crosslinked xanthan gels are disclosed in U.S. Pat. No. 4,782,901, which is herein incorporated by reference. Suitable crosslinking agents for xanthan materials include, but are not limited to: metal cations such as Al+3, Fe+3, Sb+3, Zr+4 and other transition metals. Examples of suitable commercially available xanthans include, but are not limited to: KELTROL®, KELZAN® AR, KELZAN® D35, KELZAN® S, KELZAN® XZ, available from Kelco Division of Merck, San Diego, Calif. Known organic crosslinking agents can also be used. A preferred crosslinked xanthan is KELZAN® AR, which provides a pseudo plastic use solution that can produce large particle size mist or aerosol when sprayed.

Antimicrobial Agents

Antimicrobial agents are chemical compositions that can be used to prevent microbial contamination and deterioration of commercial products. Generally, these materials fall into specific classes including, but not limited to: phenolics, halogen compounds, quaternary ammonium compounds, metal derivatives, amines, alkanol amines, nitro derivatives, analides, and organosulfur and sulfur-nitrogen compounds. The chemical composition and concentration of an antimicrobial agent may simply limit further proliferation of microbes or may destroy all or a substantial proportion of the microbial population. The terms "microbes" and "microorganisms" typically refer to bacteria and fungus microorganisms. In use, the antimicrobial agents are formed into a solid functional material that when diluted and dispensed using an aqueous stream forms an aqueous disinfectant or sanitizer composition that can be contacted with a variety of surfaces to prevent growth or kill a substantial proportion of the microbial population. A five-fold reduction of the microbial population results in a sanitizer composition.

Common antimicrobial agents include, but are not limited to: phenolic antimicrobials such as pentachlorophenol and orthophenylphenol; glutaraldehyde; propylparaben; methyl paraben; ethyl paraben; formaldehyde; benzalkonium chloride; and tetraalkylammonium chlorides or tetraalkylammonium bromides. Halogen containing antibacterial agents include, but are not limited to: sodium trichloroisocyanurate, sodium dichloroisocyanurate (anhydrous or dihydrate), iodine-poly(vinylpyrolidinonen) complexes, bromine compounds such as 2-bromo-2-nitropropane-1,3-diol quaternary antimicrobial agents such as benzalconium chloride, cetylpyridiniumchloride, amine and nitro containing antimicrobial compositions such as hexahydro-1,3,5-tris(2-hydroxyethyl)-s-triazine, and dithiocarbamates such as sodium dimethyldithiocarbamate. Exemplary commercially available antimicrobial agents include, but are not limited to: Irgasang, available from Ciba Geigy Corporation, Tarrytown, N.Y.; Neolone® and Kathon®, available from Rohm and Haas Company, Philadephia, Pa.; and Dowicil®, available from the Dow Chemical Company, Midland, Mich. Antimicrobials may be encapsulated to improve their stability and/or to reduce reactivity with other materials in the solid detergent composition.

Methods of Use

In general, a solid detergent composition using the solidification matrix of the present invention can be created by combining methacrylate, sodium carbonate, water, and any additional functional components and allowing the components to interact and solidify. For example, the solid detergent composition may include methacrylate, water, defoamer, carboxylate, sodium carbonate, metasilicate, and surfactant. In an exemplary embodiment, the solid detergent composition includes between about 1% and about 10% methacrylate by weight and preferably between about 1% and about 7% methacrylate by weight. In another exemplary embodiment, the solid detergent composition includes less than about 5% water by weight. In another exemplary embodiment, the solid detergent composition includes between about 1% and about 5% defoamer by weight and preferably between about 1% and about 3% defoamer by weight. In another exemplary embodiment, the solid detergent composition includes between about 10% and about 30% carboxylate by weight and preferably between about 15% and about 25% carboxylate by weight. In another exemplary embodiment, the solid detergent composition includes between about 15% and about 80% sodium carbonate by weight and preferably between about 20% and about 70% sodium carbonate by weight. In another exemplary embodiment, the solid detergent composition includes between about 1% and about 5% metasilicate by weight and preferably between about 2% and about 4% metasilicate by weight. In another exemplary embodiment, the solid detergent composition includes between about 1% and about 10% surfactant by weight and preferably between about 2% and about 4% surfactant by weight.

In some embodiments, the relative amounts of water and methacrylate are controlled within a composition. The solidification matrix and additional functional components harden into solid form due to the chemical reaction of the sodium carbonate with the water. As the solidification matrix solidifies, a binder composition can form to bind and solidify the components. At least a portion of the ingredients associate to form the binder while the balance of the ingredients forms the remainder of the solid composition. The solidification process may last from a few minutes to about six hours, depending on factors including, but not limited to: the size of the formed or cast composition, the ingredients of the composition, and the temperature of the composition.

Solid detergent compositions formed using the solidification matrix are produced using a batch or continuous mixing system. In an exemplary embodiment, a single- or twin-screw extruder is used to combine and mix one or more cleaning agents at high shear to form a homogeneous mixture. Preferably, the processing temperature is at or below the melting temperature of the components. The processed mixture may be dispensed from the mixer by forming, casting or other suitable means, whereupon the detergent composition hardens to a solid form. The structure of the matrix may be characterized according to its hardness, melting point, material distribution, crystal structure, and other like properties according to known methods in the art. Generally, a solid detergent composition processed according to the method of the invention is substantially homogeneous with regard to the distribution of ingredients throughout its mass and is dimensionally stable.

Specifically, in a forming process, the liquid and solid components are introduced into the final mixing system and are continuously mixed until the components form a substantially homogeneous semi-solid mixture in which the components are distributed throughout its mass. In an exemplary embodiment, the components are mixed in the mixing system for at least approximately 5 seconds. The mixture is then discharged from the mixing system into, or through, a die or other shaping means. The product is then packaged. In an exemplary embodiment, the formed composition begins to harden to a solid form in between approximately 1 minute and approximately 3 hours. Preferably, the formed composition begins to harden to a solid form in between approximately 1 minute and approximately 2 hours. More preferably, the formed composition begins to harden to a solid form in between approximately 1 minute and approximately 20 minutes.

Specifically, in a casting process, the liquid and solid components are introduced into the final mixing system and are continuously mixed until the components form a substantially homogeneous liquid mixture in which the components are distributed throughout its mass. In an exemplary embodiment, the components are mixed in the mixing system for at least approximately 60 seconds. Once the mixing is complete, the product is transferred to a packaging container where solidification takes place. In an exemplary embodiment, the cast composition begins to harden to a solid form in between approximately 1 minute and approximately 3 hours. Preferably, the cast composition begins to harden to a solid form in between approximately 1 minute and approximately 2 hours. More preferably, the cast composition or begins to harden to a solid form in between approximately 1 minute and approximately 20 minutes.

By the term "solid form", it is meant that the hardened composition will not flow and will substantially retain its shape under moderate stress or pressure or mere gravity. The degree of hardness of the solid cast composition may range from that of a fused solid block which is relatively dense and hard, for example, like concrete, to a consistency characterized as being a hardened paste. In addition, the term "solid" refers to the state of the detergent composition under the expected conditions of storage and use of the solid detergent composition. In general, it is expected that the detergent composition will remain in solid form when exposed to temperatures of up to about 100° F. and preferably greater than about 120° F.

The resulting solid detergent composition may take forms including, but not limited to: a cast solid block; an extruded, molded or formed solid pellet, block, tablet, powder, granule, flake; or the formed solid can thereafter be ground or formed into a powder, granule, or flake. In an exemplary embodiment, extruded pellet materials formed by the solidification matrix have a weight of between approximately 50 grams and approximately 250 grams, extruded solids formed by the solidification matrix have a weight of approximately 100 grams or greater, and solid block detergents formed by the solidification matrix have a mass of between approximately 1 and approximately 10 kilograms. The solid compositions provide for a stabilized source of functional materials. In some embodiments, the solid composition may be dissolved, for example, in an aqueous or other medium, to create a concentrated and/or use solution. The solution may be directed to a storage reservoir for later use and/or dilution, or may be applied directly to a point of use.

In certain embodiments, the solid detergent composition is provided in the form of a unit dose. A unit dose refers to a solid detergent composition unit sized so that the entire unit is used during a single washing cycle. When the solid detergent composition is provided as a unit dose, it is preferably provided as a cast solid, an extruded pellet, or a tablet having a size of between approximately 1 gram and approximately 50 grams.

In other embodiments, the solid detergent composition is provided in the form of a multiple-use solid, such as a block or a plurality of pellets, and can be repeatedly used to generate aqueous detergent compositions for multiple washing cycles. In certain embodiments, the solid detergent composition is provided as a cast solid, an extruded block, or a tablet having a mass of between approximately 5 grams and approximately 10 kilograms. In certain embodiments, a multiple-use form of the solid detergent composition has a mass between approximately 1 kilogram and approximately 10 kilograms. In further embodiments, a multiple-use form of the solid detergent composition has a mass of between approximately 5 kilograms and about approximately 8 kilograms. In other embodiments, a multiple-use form of the solid detergent composition has a mass of between about approximately 5 grams and approximately 1 kilogram, or between approximately 5 grams and approximately 500 grams.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

The following test method was used to characterize the compositions produced in the examples:

Dimensional Stability Test for Formed Products

Approximately 50 grams batch of the product using polymethacrylate as part of the solidification matrix was first pressed in a die at approximately 1000 pounds per square inch (psi) for approximately 20 seconds to form tablets. The diameter and height of the tablets were measured and recorded. The tablets were maintained at room temperature for one day and then placed in an oven at a temperature of approximately 120° F. After the tablets were removed from the oven, the diameters and heights of the tablets were measured and recorded. The tablets were considered to exhibit dimensional stability if there was less than approximately 2% swelling, or growth.

Dimensional Stability Test for Cast Products

Approximately 4000 grams batch of the product using polymethacrylate as part of the solidification matrix was first poured into a capsule. The diameter of the capsule was measured and recorded. The capsule was maintained at room temperature for one day, held in an oven at a temperature of approximately 104° F. for two days, and then returned to room temperature. After the capsule returned to room temperature, the diameter of the capsule was measured and recorded. The capsule was considered to exhibit dimensional stability if there was less than approximately 2% swelling, or growth.

Materials Used

Alcosperse 125, 30% active sodium polymethacrylate: a methacrylate available from ALCO Chemical Company, Chattanooga, Tenn.

Examples 1 and 2 and Comparative Example A

Examples 1 and 2 are compositions of the present invention, with component concentrations (in weight percent) of sodium carbonate (soda ash or dense ash), sodium bicarbonate, anhydrous metasilicate, carboxylate, copolymer, surfactants, Alcosperse 125 30%, and terpolymer, as provided in Table 1. The powders (sodium carbonate, sodium bicarbonate, anhydrous metasilicate, carboxylate, copolymer, surfactants) were premixed to form a powder premix and the liquids (Alcosperse 125 and terpolymer) were premixed to form a liquid premix. The powder premix and the liquid premix were then mixed together to form the composition. Approximately 50 grams of the composition were pressed into a tablet at approximately 1000 psi for approximately 20 seconds.

The composition of Comparative Example A was prepared as in Example 1, except that the composition of Comparative Example A did not include Alcosperse 125 but contained the same quantity of water.

Table 1 provides the component concentrations for the compositions of Example 1, Example 2, and Comparative Example A.

TABLE 1

| Component | Example 1 | Example 2 | Comp. Example A |
|---|---|---|---|
| Sodium carbonate, wt. % | 52.35 | 54.55 | 57.21 |
| Sodium bicarbonate, wt. % | 2.88 | 2.88 | 2.88 |
| Anhydrous metasilicate, wt. % | 3.00 | 3.00 | 3.00 |
| Carboxylate, wt. % | 20.00 | 20.00 | 20.00 |
| Copolymer, wt. % | 0.98 | 0.98 | 0.98 |
| Nonionic surfactant, wt. % | 3.53 | 3.53 | 3.53 |
| Defoamer, wt. % | 1.06 | 1.06 | 1.06 |
| Alcosperse 125, 30%, wt. % | 16.2 | 12.00 | 0.00 |
| Terpolymer, wt. % | 0.00 | 2.0 | 0.00 |
| Water, wt. % | 0.00 | 0.00 | 11.34 |

The compositions of Examples 1 and 2 and Comparative Example A were then subjected to the dimensional stability test for formed products, as discussed above, to observe the dimensional stability of the compositions after heating. The results are tabulated below in Table 2.

TABLE 2

| | | Initial | Post-heating | % Growth |
|---|---|---|---|---|
| Example 1 | Diameter, mm | 44.81 | 44.79 | 0 |
| | Height, mm | 19.15 | 19.17 | 0.1 |
| Example 2 | Diameter, mm | 44.82 | 44.87 | 0.1 |
| | Height, mm | 19.40 | 19.37 | 0.1 |
| Comparative | Diameter, mm | 44.77 | 46 | 2.7 |
| Example A | Height, mm | 19.38 | 20.96 | 8.2 |

As illustrated in Table 2, the formed products of Examples 1 and 2 exhibited considerably less swelling than the formed product of Comparative Example A. In particular, the product of Example 1 had no growth in diameter and only a 0.1% growth in height, the product of Example 2 only had a 0.1% growth in both diameter and height, while the product of Comparative Example A had a 2.7% growth in diameter and an 8.2% growth in height.

The only difference in the compositions of Examples 1 and 2 and Comparative Example A was the presence of methacrylate, Alcosperse 125. The methacrylate thus aided in the dimensional stability of the products of Example 1 and Example 2. By controlling the migration of water and acting as a donor or acceptor of free water, the methacrylate allowed processing and prevented the formed products from swelling when the products were subjected to heat as well as controlled the rate of solidification of the product within the desired range. Because the composition of Comparative Example A did not contain any methacrylate, the composition did not include a mechanism for controlling the movement of water within the solid product. Comparative Example A would not be suitable for processing and failed the test for dimensional stability.

Example 3 and Comparative Example B

Example 3 is a composition of the present invention, with component concentrations (in weight percent) of softened water, carboxylate, aminocarboxylate, Alcosperse 125 30%, polyacrylate, sodium hydroxide 50%, sodium carbonate (dense ash), anionic surfactant, and nonionic surfactant, as provided in Table 3. The liquids (softened water, aminocarboxylate, Alcosperse 125 30%, polyacrylate, and sodium hydroxide 50%) were premixed in order to form a liquid premix and the powders (sodium carbonate, anionic surfactant, and nonionic surfactant) were premixed in order to form a powder premix. The liquid premix and the powder premix were then mixed to form the composition, which was subsequently poured into capsules.

The composition of Comparative Example B was prepared as in Example 3, except that the composition of Comparative Example B did not contain any Alcosperse 125 but did contain the same quantity of available water.

Table 3 provides the composition concentrations for the compositions of Example 3 and Comparative Example B.

TABLE 3

| Component | Example 3 | Comparative Example B |
|---|---|---|
| Water, softened, wt. % | 20.49 | 27.49 |
| Carboxylate, wt. % | 4.00 | 4.00 |
| Aminocarboxylate, wt. % | 3.00 | 3.00 |
| Alcosperse 125, 30%, wt. % | 10.00 | 0.00 |
| Polyacrylate, wt. % | 0.75 | 0.75 |
| NaOH, 50%, wt. % | 0.33 | 0.33 |
| Sodium carbonate, wt. % | 56.43 | 59.43 |
| Anionic surfactant, wt. % | 1.00 | 1.00 |
| Nonionic surfactant, wt. % | 4.00 | 4.00 |

After the compositions of Example 3 and Comparative Example B were formed, they were subjected to the dimensional stability test for cast products, as discussed above, to observe the dimensional stability of the compositions after heating. The results are tabulated below in Table 4.

TABLE 4

| | | Initial | Post-heating | % Growth |
|---|---|---|---|---|
| Example 3 | Diameter, mm | 161 | 163 | 1.2 |
| Comparative Example B | Diameter, mm | 161 | 170 | 5.6 |

As illustrated in Table 4, the cast product of Example 3 exhibited considerably less swelling than the cast product of Comparative Example B. In particular, the product of Example 3 experienced only a 1.2% growth in diameter, while the product of Comparative Example B had a 5.6% growth in diameter.

The only difference in the compositions of Example 3 and Comparative Example B was the presence of methacrylate, Alcosperse 125. The methacrylate thus aided in the dimensional stability of the products of Example 3. By controlling the migration of water and acting as a donor or acceptor of free water, the methacrylate allowed processing and prevented the cast product from swelling when the product was subjected to heat as well as controlled the rate of solidification of the product within the desired range. By contrast, because the composition of Comparative Example B did not contain any methacrylate, the composition did not contain a mechanism for controlling the movement of water within the solid product. The composition of Comparative Example B failed the test for dimensional stability and would not be suitable for manufacture.

Although the present invention has been described with reference to preferred embodiments, workers skilled in the art will recognize that changes may be made in form and detail without departing from the spirit and scope of the invention.

The invention claimed is:

1. A solidification matrix consisting essentially of:

(a) methacrylate;

(b) sodium carbonate; and (c) water;

(d) wherein the methacrylate, sodium carbonate, and water interact to form a hydrate solid;

(e) wherein if heated at a temperature of 120 degrees Fahrenheit, the solidification matrix is dimensionally stable and has a growth exponent of less than 2%; and (f) wherein the solidification matrix is substantially phosphorus-free.

2. The solidification matrix of claim 1, wherein the methacrylate is selected from the group consisting of: sodium polymethacrylate, lithium polymethacrylate, potassium polymethacrylate, ammonium polymethacrylate, and alkanolamine polymethacrylates.

3. The solidification matrix of claim 1, wherein the methacrylate constitutes between about 1% and about 10% by weight of the solidification matrix.

4. The solidification matrix of claim 3, wherein the methacrylate constitutes between about 1% and about 7% by weight of the solidification matrix.

5. The solidification matrix of claim 1, wherein the sodium carbonate constitutes between about 15% and about 80% by weight of the solidification matrix.

6. The solidification matrix of claim 5, wherein the sodium carbonate constitutes between about 20% and about 70% by weight of the solidification matrix.

7. The solidification matrix of claim 1, wherein the solidification matrix comprises less than about 0.5% nitrilotriacetic acid.

8. The solidification matrix of claim 1, and further comprising at least one functional ingredient selected from the group consisting of: chelating agents, sequestering agents, inorganic detergents, organic detergents, alkaline sources, surfactants, cleaning agents, rinse aids, bleaching agents, sanitizers, anti-microbial agents, activators, detergent builders, fillers, defoaming agents, anti-redeposition agents, optical brighteners, dyes, odorants, secondary hardening agents, and solubility modifiers.

9. A method of solidifying a composition, the method comprising:

(a) adding a solidification matrix consisting essentially of methacrylate, sodium carbonate, and water, wherein the solidification matrix is substantially phosphorus-free; and (b) solidifying the composition for between about 1 minute and about 3 hours to form a solid composition that, if subjected to a temperature of 120 degrees Fahrenheit, is dimensionally stable and has a growth exponent of less than 2%.

10. The method of claim 9, and further comprising forming the material into a block.

11. The method of claim 9, and further comprising casting the material into a packaging container.

12. The method of claim 9, wherein the block solidifies in between about 1 minute and about 2 hours.

13. The method of claim 9, wherein the material in the packing container solidifies in between about 1 minute and about 20 minutes.

* * * * *